(12) United States Patent
Banna et al.

(10) Patent No.: US 11,781,100 B2
(45) Date of Patent: Oct. 10, 2023

(54) ALL-IN-ONE BIOREACTOR FOR THERAPEUTIC CELLS MANUFACTURING

(71) Applicant: Applied Materials, Inc., Santa Clara, CA (US)

(72) Inventors: Samer Banna, San Jose, CA (US); Mukhles Sowwan, Cupertino, CA (US); Gary E. Dickerson, Cupertino, CA (US)

(73) Assignee: APPLIED MATERIALS, INC., Santa Clara, CA (US)

( * ) Notice: Subject to any disclaimer, the term of this patent is extended or adjusted under 35 U.S.C. 154(b) by 0 days.

(21) Appl. No.: 17/111,359

(22) Filed: Dec. 3, 2020

(65) Prior Publication Data

US 2022/0177821 A1    Jun. 9, 2022

(51) Int. Cl.
*C12M 3/00* (2006.01)
*C12M 1/00* (2006.01)

(52) U.S. Cl.
CPC ............ *C12M 23/44* (2013.01); *C12M 23/26* (2013.01); *C12M 23/58* (2013.01); *C12M 29/18* (2013.01)

(58) Field of Classification Search
CPC ...... C12M 23/44; C12M 23/26; C12M 23/58; C12M 29/18
See application file for complete search history.

(56) References Cited

U.S. PATENT DOCUMENTS

| 9,266,725 B2 | 2/2016 | VanDersarl et al. |
| 2007/0172944 A1 | 7/2007 | Li |
| 2014/0178992 A1 | 6/2014 | Nakashima et al. |
| 2017/0175139 A1 | 6/2017 | Wu et al. |
| 2019/0211294 A1* | 7/2019 | Karnieli ................. C12M 41/48 |

FOREIGN PATENT DOCUMENTS

| CN | 104087509 A | 10/2014 |
| CN | 109142712 B | 11/2019 |
| WO | WO 2013-088147 A1 | 6/2013 |
| WO | WO 2017-214541 A1 | 12/2017 |
| WO | WO 2019/946766 A2 | 3/2019 |

OTHER PUBLICATIONS

PCT International Search Report and Written Opinion for PCT/US2021/061495 dated Mar. 18, 2022.

* cited by examiner

*Primary Examiner* — William H. Beisner
*Assistant Examiner* — Danielle B Henkel
(74) *Attorney, Agent, or Firm* — MOSER TABOADA

(57) ABSTRACT

Methods and apparatus of bioreactors for therapeutic cells manufacturing are provided herein. In some embodiments, a bioreactor includes: an upper bioreactor reservoir configured to perform multiple cell therapy manufacturing process steps including genetic modification and expansion to a plurality of cells disposed therein, wherein the upper bioreactor reservoir includes a plurality of ports for delivering fluids into and out of the upper bioreactor reservoir; a lower bioreactor compartment configured to hold a suspension comprising a molecular species; and a membrane disposed between the lower bioreactor compartment and the upper bioreactor reservoir, wherein the membrane includes a plurality of micro-straws extending through the membrane and into the upper bioreactor reservoir to transfect the plurality of cells with the molecular species.

19 Claims, 3 Drawing Sheets

US 11,781,100 B2

ALL-IN-ONE BIOREACTOR FOR THERAPEUTIC CELLS MANUFACTURING

FIELD

Embodiments of the present disclosure generally relate to cell therapy equipment, and more specifically, a multifunctional bioreactor for cell therapy manufacturing.

BACKGROUND

Cell therapy is the introduction of cells into a patient's body to repair damaged tissue or treat a disease. A variety of cells can be used in cell therapy including lymphocytes (such as T cells), dendritic cells, and stem cells. The source of the cells can be from the patient's own body (autologous) or from a donor (allogenic). In some cases, cells are genetically modified (for example CAR-T gene modified cell therapy) before being reintroduced to the patient. In CAR-T, cells are collected from the blood, then genetically modified to present receptors called Chimeric Antigen Receptors (CARs) on their surface. The cells are then expanded to reach a required dose. When these modified cells are reinfused into the patient, the CAR receptors enable the modified cells to recognize specific antigens on the tumor cells and kill them.

A bioreactor is a multifunctional vessel that may be used in several steps during the cell therapy manufacturing process. Example of such manufacturing steps include cell activation, genetic modification and expansion. Genetic modification is the process of altering the genetic make-up of a cell. Although possible to perform genetic modification of the cells inside the bioreactor using a number of viral (transduction) or non-viral (transfection) methods, conventional bioreactors do not have the physical mechanism for genetic modification of cells via a direct delivery of molecular species into the cytosol or nucleus of the cells without routing the cells to an external apparatus, compromising the cells viability, health and function. Thus, the inventors have provided improved bioreactors for cell therapy manufacturing.

SUMMARY

Methods and apparatus of bioreactors for therapeutic cells manufacturing are provided herein. In some embodiments, a bioreactor includes: an upper bioreactor reservoir configured to perform multiple cell therapy manufacturing process steps including genetic modification and expansion to a plurality of cells disposed therein, wherein the upper bioreactor reservoir includes a plurality of ports for delivering fluids into and out of the upper bioreactor reservoir; a lower bioreactor compartment configured to hold a suspension comprising a molecular species; and a membrane disposed between the lower bioreactor compartment and the upper bioreactor reservoir, wherein the membrane includes a plurality of micro-straws extending through the membrane and into the upper bioreactor reservoir to transfect the plurality of cells with the molecular species.

In some embodiments, a method of performing a transfection process and an expansion process to a plurality of cells in a bioreactor includes: flowing a first cell culture media into an upper reservoir of the bioreactor having a plurality of cells disposed therein via a fluid input port of the upper reservoir; flowing a transfection media or suspension comprising a molecular species for genetically modifying the plurality of cells through a lower compartment of the bioreactor, wherein the upper reservoir and the lower compartment are separated by a membrane having a plurality of micro-straws extending therethrough; performing a transfection process to the plurality of cells in the upper reservoir by injecting the molecular species from the transfection media or suspension into the plurality of cells via the plurality of micro-straws to form a plurality of genetically modified cells; and expanding the plurality of genetically modified cells in the upper reservoir via the first cell culture media.

In some embodiments, a non-transitory computer readable medium having instructions stored thereon that, when executed by a processor, causes a bioreactor to perform a method includes: flowing a first cell culture media into an upper reservoir of the bioreactor having a plurality of cells disposed therein via a fluid input port of the upper reservoir; flowing a transfection media or suspension comprising a molecular species for genetically modifying the plurality of cells through a lower compartment of the bioreactor, wherein the upper reservoir and the lower compartment are separated by a membrane having a plurality of micro-straws extending therethrough; performing a transfection process to the plurality of cells in the upper reservoir by injecting the molecular species from the transfection media or suspension into the plurality of cells via the plurality of micro-straws to form a plurality of genetically modified cells; and expanding the plurality of genetically modified cells in the upper reservoir via the first cell culture media.

Other and further embodiments of the present disclosure are described below.

BRIEF DESCRIPTION OF THE DRAWINGS

Embodiments of the present disclosure, briefly summarized above and discussed in greater detail below, can be understood by reference to the illustrative embodiments of the disclosure depicted in the appended drawings. However, the appended drawings illustrate only typical embodiments of the disclosure and are therefore not to be considered limiting of scope, for the disclosure may admit to other equally effective embodiments.

Figure 1:
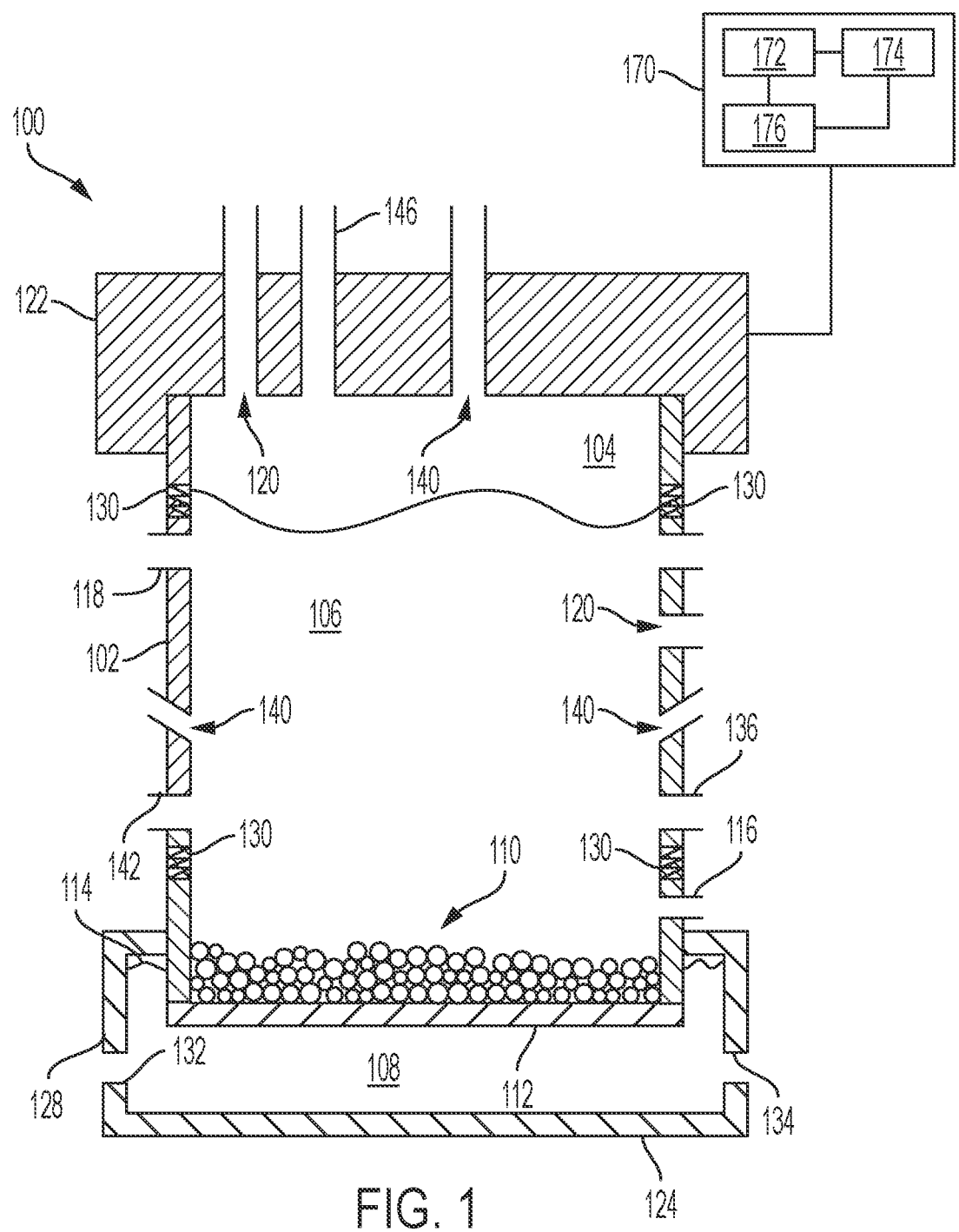
FIG. 1 depicts a schematic cross-sectional view of a bioreactor in accordance with some embodiments of the present disclosure.

To facilitate understanding, identical reference numerals have been used, where possible, to designate identical elements that are common to the figures. The figures are not drawn to scale and may be simplified for clarity. Elements and features of one embodiment may be beneficially incorporated in other embodiments without further recitation.

DETAILED DESCRIPTION

Methods and apparatus of bioreactors for expanding therapeutic cells are provided herein. The bioreactors provided herein are bioreactors configured to advantageously perform genetic modification and expansion processes on a plurality of cells disposed in a bioreactor reservoir. The advantages of such a configuration over conventional bioreactors include but are not limited to: (1) enabling genetic modification of the cells by direct delivery of molecular species into the cytosol or nucleus of the cells in an optimized macro-environment (i.e., inside the bioreactor without routing the cells to an external apparatus which might compromise the cells' viability, health, and function); (2) enabling a fast genetic modification step at scale inside the bioreactor due to the high surface area of the membrane; (3) allowing for in situ monitoring of the metabolism of the plurality of cells during a genetic modification step using a set of sensors integrated on the bioreactor ports and adjusting a cell culture condition accordingly (either manually or using an automated artificial intelligence (A.I.) or machine learning techniques) to optimize the genetic modification process; and (4) enables a universal all-in-one cell manufacturing system for point-of-care cell therapy.

In some embodiments, the bioreactor is part of a multi-process platform. In some embodiments, the bioreactor is a single use system. By performing both the genetic modification and the expansion processes in the bioreactor reservoir, the plurality of cells advantageously don't need to be removed from an optimized environment between the genetic modification and the expansion processes. The bioreactor may advantageously be portable and used at a point of care in a hospital or clinical setting.

Genetic modification may be performed via a transfection process, where the plurality of cells are modified using a non-viral method through the delivery of molecular species across a lipid bilayer of the plurality of cells and into a cytosol or nucleus of the plurality of cells. The transfection process may be used to deliver a large load of molecular species. The expansion process increases the modified plurality of cells to a desired dose. The plurality of cells may be any cell suitable for use in gene therapy, for example, primary cells such as T-cells, stem cells, adherent cells, suspension cells, or the like.

The molecular species may be one or more of DNA, RNA, mRNA, siRNA, CRISPR-Cas, Zinc finger, TALENs, or the like. DNA is generally a molecule composed of double-stranded polynucleotide chains in a helix pattern that carry genetic instructions. RNA is generally a single-stranded polynucleotide chain folded onto itself rather than a paired double strand. Messenger RNA (mRNA) is a single-stranded RNA molecule that is complementary to one of the DNA strands of a gene. Small interfering RNA (siRNA) is a double stranded non-coding RNA molecule. The clustered regularly interspaced short palindromic repeats (CRISPR)-Cas (CRISPR-associated proteins) is a prokaryotic adaptive immune system that is represented in most archaea and many bacteria. A zinc finger is a small protein molecule that is characterized by the coordination of one or more zinc ions (Zn2+) in order to stabilize the molecule into several different structural families. Typically, the vast majority of structural families function as interaction modules that bind DNA, RNA, proteins, or other small, useful molecules, to alter the binding specificity of a particular protein. Transcription activator-like effector nucleases (TALEN) are restriction enzymes that can be engineered to cut specific sequences of DNA.

FIG. 1 depicts a schematic cross-sectional view of a bioreactor in accordance with some embodiments of the present disclosure. The bioreactor 100 generally comprises an upper bioreactor reservoir 104, a lower bioreactor compartment 108, and a membrane 112 disposed therebetween. In some embodiments, the bioreactor 100 is cylindrical, conical, or cube shaped. The bioreactor 100 may be made of a suitable material for processing a plurality of cells 110 disposed therein. For example, in some embodiments, the bioreactor 100 is made of glass or thermoplastic, such as biocompatible thermoplastic.

The upper bioreactor reservoir 104 is configured to perform multiple cell therapy manufacturing process steps to the plurality of cells 110 disposed therein. Multiple cell therapy process steps may include activation, genetic modification, and expansion processes to the plurality of cells 110. The upper bioreactor reservoir 104 includes a plurality of ports 120 for delivering fluids into and out of the upper bioreactor reservoir. In some embodiments, the plurality of ports 120 include a fluid input port 118 and a fluid drain port 116. The fluid input port 118 is configured to deliver the plurality of cells 110, a first cell culture media 106 that includes nutrition for the plurality of cells 110, or the first cell culture media 106 that includes the plurality of cells. The fluid drain port 116 is configured to the drain the first cell culture media 106 from the upper bioreactor reservoir 104.

In some embodiments, the upper bioreactor reservoir 104 is defined between the membrane 112, the upper sidewalls 102 extending upward from the membrane 112, and a lid 122 disposed atop the upper sidewalls 102. In some embodiments, the upper bioreactor reservoir 104 has a capacity of about 0.5 liters to about 5.0 liters. In some embodiments, the upper bioreactor reservoir 104 is expandable. For example, the upper sidewalls 102 of the upper bioreactor reservoir 104 may include a plurality of expandable members 130 configured to selectively expand or contract based on pressure in the upper bioreactor reservoir 104. In some embodiments, the upper bioreactor reservoir 104 is cylindrical, conical, or cube shaped. A conical shaped upper bioreactor reservoir 104 may advantageously provide increased volume for the plurality of cells 110 to expand into when they undergo an expansion process.

The bioreactor 100 includes a lower bioreactor compartment 108 configured to hold a transfection media 114 comprising a liquid or suspension. In some embodiments, the transfection media 114 includes a molecular species for genetically modifying the plurality of cells 110. In some embodiments, the lower bioreactor compartment 108 is defined between the membrane 112, a bottom plate 124 of the bioreactor 100, and lower sidewalls 128. The lower bioreactor compartment 108 may include an input port 132 and an output port 134 to flow the transfection media 114 through the lower bioreactor compartment 108 to replenish the transfection media 114. In some embodiments, the input port 132 is disposed on one side of the lower sidewalls 128 and the output port 134 is disposed on another side of the lower sidewalls 128 opposite the input port 132.

Figure 2:
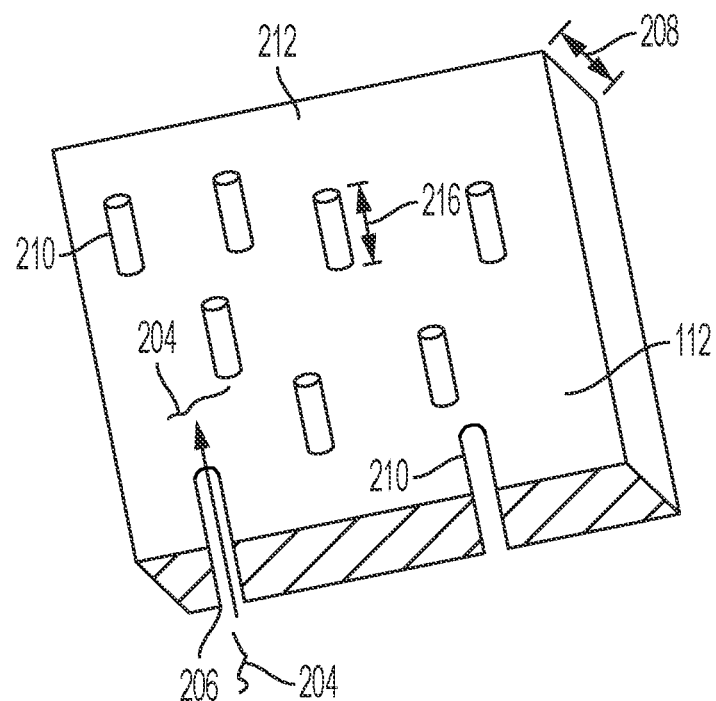
FIG. 2 depicts an isometric cross-sectional view of a membrane of a bioreactor in accordance with some embodiments of the present disclosure.

A membrane 112 is disposed between the lower bioreactor compartment 108 and the upper bioreactor reservoir 104. The plurality of cells 110 when disposed in the upper bioreactor reservoir 104, rest on the membrane 112. FIG. 2 depicts an isometric cross-sectional view of the membrane 112 in accordance with some embodiments of the present disclosure. The membrane 112 includes a plurality of microstraws 210 extending through the membrane 112 and into the upper bioreactor reservoir 104 to transfect the plurality of cells 110 with a molecular species 204. The molecular species 204 may comprise at least one of DNA, RNA mRNA, siRNA, CRISPR-Cas, Zinc finger, TALENs, or the like. In some embodiments, the membrane 112 comprises a polymer or a silicon film. In some embodiments, the membrane 112 is made of a polycarbonate. In some embodiments, a thickness 208 of the membrane 112 is about 4.0 to about 100.0 micrometers.

Each of the micro-straws 210 include a duct 206 for fluidly coupling the upper bioreactor reservoir 104 and the lower bioreactor compartment 108 and facilitating the transfer of the molecular species 204 into the plurality of cells 110. In some embodiments, the micro-straws 210 are made of a metal oxide, for example, alumina. The micro-straws 210 may have any suitable cross-sectional shape for piercing the plurality of cells 110. In some embodiments, the micro-straws 210 have a cylindrical, conical, or rectangular prism shape. In some embodiments, a height 216 of the micro-straws 210 from a surface 212 of the membrane 112 is about 0.5 to about 3.0 micrometers. In some embodiments, a density of the micro-straws 210 on the membrane 112 is about $10^4$ to about $10^9$ micro-straws per square centimeter. The density of the micro-straws 210 may advantageously be greater than a density of the plurality of cells 110 to more easily pierce the plurality of cells 110. In some embodiments, a diameter of the micro-straws 210 is about 0.05 micrometers to about 0.2 micrometers.

Referring back to FIG. 1, the plurality of ports 120 of the upper bioreactor reservoir 104 include one or more sensor ports 140 configured to integrate the bioreactor with at least one of a carbon dioxide ($CO_2$) sensor, an oxygen ($O2$) sensor, a pH sensor, a glucose sensor, a lactate sensor, a lactose sensor, glutamine sensor, or a temperature sensor. The one or more sensor ports 140 are configured to monitor and control (for example, through A.I. or machine learning techniques) respective levels of one or more of $CO_2$, O2, pH, glucose, lactate, lactose, glutamine, or temperature to create an optimized or desired environment for genetic modification or expansion of the plurality of cells 110.

In some embodiments, the one or more sensor ports 140 are disposed in the upper sidewalls 102. In some embodiments, the one or more sensor ports 140 are disposed in both the upper sidewalls 102 and the lid 122. For example, a glucose sensor may be integrated with a port of the one or more sensor ports 140 in the lid 122 and a carbon dioxide ($CO_2$) sensor and an oxygen ($O2$) sensor may be integrated with ports of the one or more sensor ports 140 disposed in the upper sidewalls 102. In some embodiments, the one or more sensor ports 140 are disposed in the lid 122 only.

In some embodiments, the plurality of ports 120 of the upper bioreactor reservoir 104 include a collection port 136 configured to harvest the plurality of cells 110. In some embodiments, the collection port 136 is disposed in the upper sidewalls 102. In some embodiments, the plurality of ports 120 of the upper bioreactor reservoir 104 include one or more gas exchange ports 142. The one or more gas exchange ports 142 are configured to deliver or remove gases such as oxygen ($O2$) or carbon dioxide ($CO_2$) into the upper bioreactor reservoir 104 to promote expansion of the plurality of cells 110, for example, by controlling a pH of the first cell culture media 106.

In some embodiments, one or more of the plurality of ports 120 are device ports 146 disposed in the lid 122 and configured to integrate the bioreactor 100 with at least one of an optical microscope, a stirrer, one or more metal electrodes, or a camera. The stirrer, for example, may comprise a propeller for mixing the first cell culture media 106 to mix nutrients therein and keep the first cell culture media 106 more homogenous. The optical microscope or camera may be used to monitor the morphology and viability of the plurality of cells 110. The one or more metal electrodes may be used for the application of short electrical pulses to cause a reversible breakdown of the cells membrane and facilitate the uptake of the molecular species.

The bioreactor 100 may include a controller 170 for processing control programs, such as A.I. or machine learning algorithms. The controller 170 generally controls the operation of the bioreactor 100. The controller 170 may also control respective levels of one or more of $CO_2$, O2, pH, glucose, lactate, lactose, glutamine, or temperature to create an optimized or desired environment for genetic modification or expansion of the plurality of cells 110. The controller 170 generally includes a central processing unit (CPU) 172, a memory 174, and a support circuit 176. The CPU 172 may be one of any form of a general-purpose computer processor that can be used in an industrial setting. The support circuit 176 is conventionally coupled to the CPU 172 and may comprise a cache, clock circuits, input/output subsystems, power supplies, and the like. Software routines, such as processing methods as described herein may be stored in the memory 174 and, when executed by the CPU 172, transform the CPU 172 into a specific purpose computer (controller 170).

In operation, the controller 170 enables data collection and feedback from various sensors, devices, or the like, that are coupled to the bioreactor 100 to optimize therapeutic cell manufacturing and provides instructions to system components. For example, the memory 174 can be a non-transitory computer readable medium having instructions stored thereon that, when executed by the CPU 172 (or controller 170), cause the methods described herein to be performed. For example, the controller 170 can collect data from sensors, devices, or the like, that are coupled to the bioreactor via the plurality of ports 120 and instruct the bioreactor 100 to perform a suitable process.

In some embodiments, suitable A.I. or machine learning techniques can be applied to learn commonalities in sequential application programs and for determining from the A.I. or machine learning techniques at what level sequential application programs can be canonicalized. In some embodiments, machine learning techniques that can be applied to learn commonalities in sequential application programs can include, but are not limited to, regression methods, ensemble methods, or neural networks and deep learning such as 'Se2oSeq' Recurrent Neural Network (RNNs)/Long Short Term Memory (LSTM) networks, graph neural networks applied to the abstract syntax trees corresponding to the sequential program application.

In some embodiments, the A.I. or machine learning techniques may receive data inputs from sensors and devices associated with the bioreactor 100, along with user inputs. In some embodiments, the A.I. or machine learning techniques may receive data inputs as imported data files. For example, data inputs may be derived from 'Omics' technologies such as sequencing or mass spectrometers (offline characterization) which are imported as data files before or during manufacturing of cells using the methods and apparatus described herein. The data collected from one or more of the above sources can be partially, or fully, combined to train the machine learning model.

The A.I. or machine learning techniques may be used to refine parameters of the bioreactor 100 as the plurality of cells 110 are genetically modified, expanded, and harvested. For example, metabolomics can be performed real time on the plurality of cells 110 allowing for a prediction of how much the cells will expand as a function of time, and the machine learning techniques may be used to determine how to adjust the experimental conditions (e.g., regulate nutrients, $CO_2$, $O2$, pH, glucose, lactate, lactose, glutamine, or temperature) to meet certain cell expansion thresholds for the plurality of cells 110.

Figure 3:
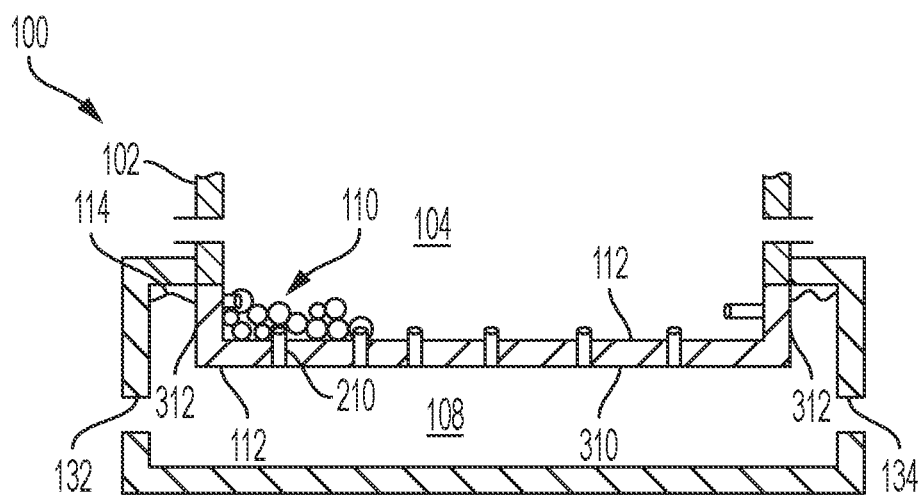
FIG. 3 depicts a schematic cross-sectional view of a portion of a bioreactor in accordance with some embodiments of the present disclosure.

FIG. 3 depicts a schematic cross-sectional view of a portion of a bioreactor in accordance with some embodiments of the present disclosure. In some embodiments, the membrane 112 includes a horizontal portion 310 and vertical portions 312 extending upward from sides of the horizontal portion 310 to advantageously increase a surface area of the membrane 112 exposed to the plurality of cells 110. An increased surface area of the membrane 112 exposed to the plurality of cells 110 may increase rate of genetic modification of the plurality of cells 110 and increase efficiency of the bioreactor 100. For example, cells of the plurality of cells 110 adjacent the vertical portions 312 may be pierced with the micro-straws 210 extending form the vertical portions 312 and into the upper bioreactor reservoir 104. In some embodiments, the upper sidewalls 102 of the upper bioreactor reservoir 104 include the vertical portions 312. In some embodiments, the vertical portions 312 extend to a location between the horizontal portion 310 and the lid 122. In some embodiments, the vertical portions 312 extend to a location between the horizontal portion 310 and any ports of the plurality of ports 120. In some embodiments, the vertical portions 312 extend from the horizontal portion 310 to the lid 122. In some embodiments, one or more of the plurality of ports 120 extend through vertical portions 312 of the membrane 112.

Figure 4:
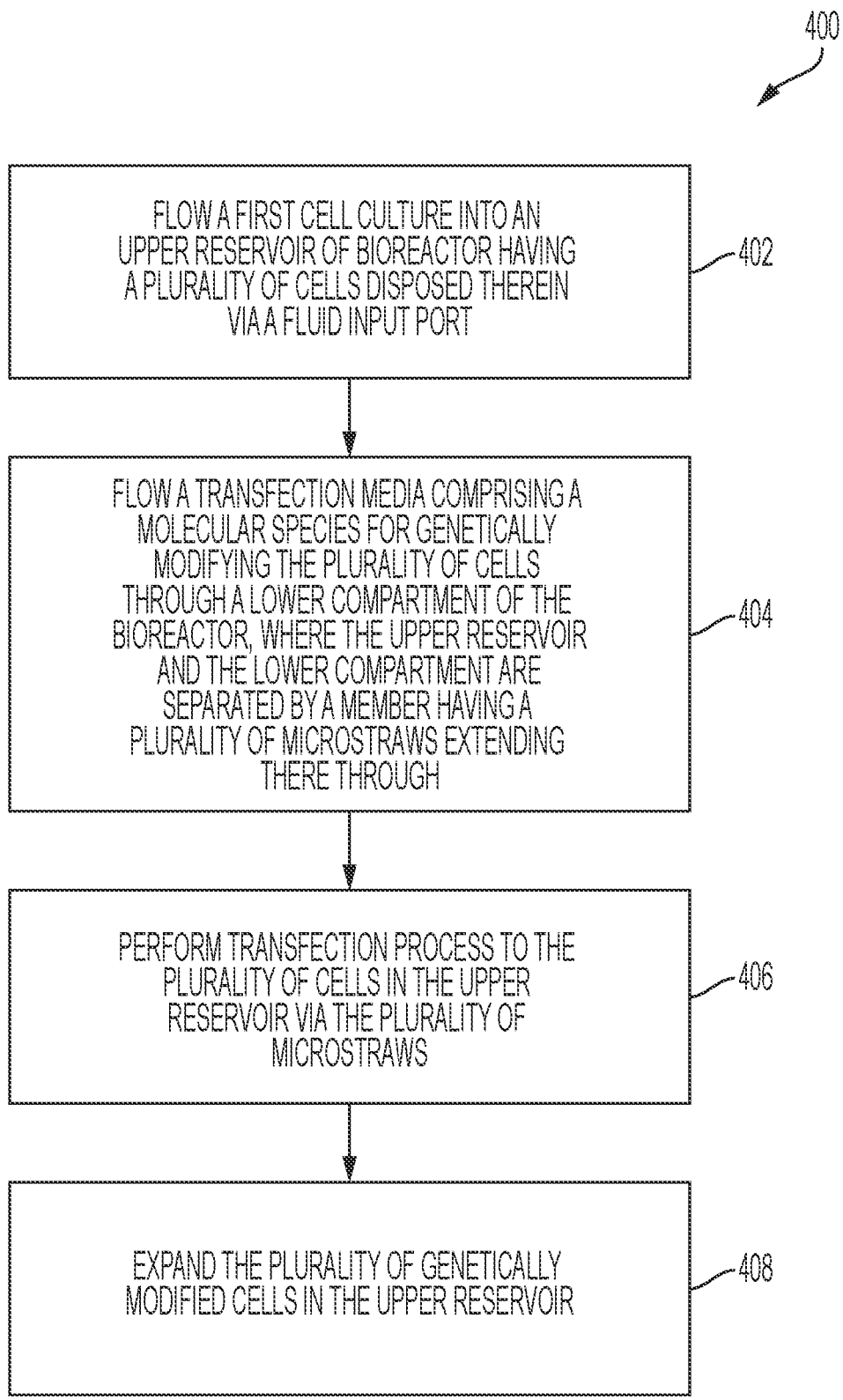
FIG. 4 depicts a flow chart of a method of performing a transfection process and an expansion process to a plurality of cells in a bioreactor in accordance with some embodiments of the present disclosure.

FIG. 4 depicts a flow chart of a method 400 of performing a transfection process and an expansion process to a plurality of cells (i.e., plurality of cells 110) in a bioreactor (i.e., bioreactor 100) in accordance with some embodiments of the present disclosure. The plurality of cells are disposed in an upper reservoir (i.e., upper bioreactor reservoir 104) of the bioreactor. In some embodiments, the plurality of cells comprise at least one of primary cells, stem cells, adherent cells, or suspension cells.

At 402, a first cell culture media (i.e., first cell culture media 106) is flowed into the upper reservoir of the bioreactor having the plurality of cells disposed therein via a fluid input port (i.e., fluid input port 118) of the upper reservoir. The fluid input port 118 may be disposed in upper sidewalls (i.e. upper sidewalls 102) or a lid (i.e. lid 122) of the bioreactor.

At 404, a transfection media (i.e., transfection media 114) comprising a molecular species (i.e., molecular species 204) for genetically modifying the plurality of cells is flowed through a lower compartment (i.e., lower bioreactor compartment 108) of the bioreactor. In some embodiments, the molecular species comprises at least one of DNA, RNA, mRNA, siRNA, CRISPR-Cas, Zinc finger, TALENs, or the like. The upper reservoir and the lower compartment are separated by a membrane (i.e., membrane 112) having a plurality of micro-straws (i.e., micro-straws 210) extending through the membrane. In some embodiments, a density of the plurality of micro-straws is greater than a density of the plurality of cells so that the micro-straws pierce the plurality of cells.

At 406, a transfection process is performed on the plurality of cells in the upper reservoir by injecting the molecular species from the transfection media into the plurality of cells via the plurality of micro-straws to form a plurality of genetically modified cells. The transfection media may be replenished or recirculated through the lower bioreactor compartment via an input port (i.e., input port 132) and output port (i.e., output port 134) so that the molecular species is not depleted from the transfection media.

At 408, the plurality of genetically modified cells are expanded in the upper reservoir via the first cell culture media. In some embodiments, the first cell culture media includes at least one of amino acids, vitamins, fatty acids, nutrition, or lipids to expand the plurality of genetically modified cells. In some embodiments, the first cell culture media is compatible with the transfection media. In some embodiments, the upper bioreactor reservoir may be expandable to accommodate the expanded plurality of modified cells. For example, in some embodiments, the upper bioreactor reservoir may expand about 30 percent to about 100 percent in volume.

In some embodiments, a portion of the first cell culture media is drained from the upper reservoir via a fluid drain port (i.e., fluid drain port 116) prior to performing the transfection process to the plurality of cells. This may ensure that more cells of the plurality of cells rest on or against the membrane rather than suspended in the first cell culture media. In some embodiments, about 50 percent to about 90 percent of the first cell culture media is drained prior to performing the transfection process. In some embodiments, the transfection process comprises injecting the molecular species from the transfection media to a first subset of the plurality of cells resting on the membrane, adding additional first cell culture media to the upper reservoir to mix the plurality of cells, draining at least a portion of a remaining first cell culture media from the upper reservoir so that a second subset of the plurality of cells rests on the membrane, and injecting the molecular species from the transfection media to the second subset of the plurality of cells. This process may be repeated until a desired number or percentage of the plurality of cells are modified.

In some embodiments, the bioreactor may also perform at least one of an activation process, a concentration process, or a wash and harvest process. The activation process comprises using an activation reagent for a downstream step. The concentration process comprises concentrating the plurality of cells before or after expansion. The wash and harvest process comprises washing the concentrated or expanded plurality of cells and harvesting the concentrated plurality of cells.

While the foregoing is directed to embodiments of the present disclosure, other and further embodiments of the disclosure may be devised without departing from the basic scope thereof.

The invention claimed is:

1. A bioreactor, comprising:
an upper bioreactor reservoir configured to perform multiple cell therapy manufacturing process steps including genetic modification and expansion to a plurality of cells disposed therein, wherein the upper bioreactor reservoir includes a plurality of ports for delivering fluids into and out of the upper bioreactor reservoir;
a lower bioreactor compartment configured to hold a suspension comprising a molecular species; and
a membrane disposed between the lower bioreactor compartment and the upper bioreactor reservoir, wherein the membrane includes a plurality of micro-straws extending through the membrane and into the upper bioreactor reservoir to transfect the plurality of cells with the molecular species, wherein the membrane includes a horizontal portion and vertical portions extending upward from sides of the horizontal portion, wherein the plurality of micro-straws are disposed along the horizontal portion and the vertical portions, wherein sidewalls of the upper bioreactor reservoir include the vertical portions.

2. The bioreactor of claim 1, wherein the upper bioreactor reservoir includes a fluid input port and the lower bioreactor compartment includes an input port that is fluidly independent of the fluid input port of the upper bioreactor reservoir.

3. The bioreactor of claim 1, wherein the upper bioreactor reservoir is expandable.

4. The bioreactor of claim 1, wherein the membrane comprises a polymer or a silicon film.

5. The bioreactor of claim 1, wherein at least one of:
a thickness of the membrane is about 4.0 to about 100.0 micrometers; or
a height of the micro-straws from a surface of the membrane is about 0.5 to about 3.0 micrometers.

6. The bioreactor of claim 1, wherein the lower bioreactor compartment is fluidly coupled to a source of transfection media, and wherein the upper bioreactor reservoir is coupled to a source of a first cell culture media.

7. The bioreactor of claim 1, wherein a density of the micro-straws on the membrane is about $10^4$ to about $10^9$ micro-straws per square centimeter.

8. The bioreactor of claim 1, wherein an upper surface of the lower bioreactor compartment extends vertically above the membrane.

9. The bioreactor of claim 1, wherein the upper bioreactor reservoir is defined between the membrane, upper sidewalls extending upward from the membrane, and a lid disposed atop the upper sidewalls.

10. The bioreactor of claim 9, wherein a plurality of ports are disposed in the upper sidewalls and the lid.

11. The bioreactor of claim 9, wherein one or more of a plurality of ports are disposed in an upper surface of the lid.

12. The bioreactor of claim 1, wherein the lower bioreactor compartment is defined between the membrane, a bottom plate of the bioreactor, and lower sidewalls.

13. The bioreactor of claim 1, wherein the bioreactor is cylindrical, conical, or cube shaped.

14. The bioreactor of claim 1, wherein the upper bioreactor reservoir has a capacity of about 0.5 liters to about 5.0 liters.

15. The bioreactor of claim 1, wherein the bioreactor is made of biocompatible thermoplastic or glass.

16. The bioreactor of claim 1, wherein the membrane is made of a polycarbonate and the micro-straws are made of alumina.

17. A bioreactor, comprising:
an upper bioreactor reservoir configured to perform multiple cell therapy manufacturing process steps including genetic modification and expansion to a plurality of cells disposed therein, wherein the upper bioreactor reservoir includes a plurality of ports for delivering fluids into and out of the upper bioreactor reservoir, wherein the plurality of ports include a fluid input port, a fluid drain port, one or more gas exchange ports, and a collection port configured to harvest the plurality of cells;
a lower bioreactor compartment configured to hold a suspension comprising a molecular species; and
a membrane disposed between the lower bioreactor compartment and the upper bioreactor reservoir, wherein the membrane includes a plurality of micro-straws extending through the membrane and into the upper bioreactor reservoir to transfect the plurality of cells with the molecular species, wherein the upper bioreactor reservoir is fluidly separated from the lower bioreactor compartment except through the plurality of micro-straws, and wherein the membrane includes a horizontal portion and vertical portions extending upward from sides of the horizontal portion, wherein the plurality of micro-straws are disposed along the horizontal portion and the vertical portions, wherein sidewalls of the upper bioreactor reservoir include the vertical portions.

18. The bioreactor of claim 17, wherein the fluid input port and the fluid drain port are both disposed through sidewalls of the upper bioreactor reservoir.

19. The bioreactor of claim 17, wherein the plurality of ports of the upper bioreactor reservoir include one or more sensor ports configured to integrate the bioreactor with at least one of a carbon dioxide ($CO_2$) sensor, an oxygen ($O_2$) sensor, a pH sensor, a glucose sensor, a lactate sensor, a lactose sensor, or a glutamine sensor.

* * * * *